United States Patent [19]
Johnson et al.

[11] Patent Number: 5,763,492
[45] Date of Patent: Jun. 9, 1998

[54] METHODS FOR EFFECTING MEMORY ENHANCEMENT MEDIATED BY NON-STEROIDAL SULFATASE INHIBITORS

[75] Inventors: David A. Johnson, Butler; Pui-Kai Li, Library, both of Pa.

[73] Assignee: Duquesne University of the Holy Ghost, Pittsburgh, Pa.

[21] Appl. No.: 722,740

[22] Filed: Oct. 1, 1996

[51] Int. Cl.⁶ .......................... A61K 31/18; A61K 31/56
[52] U.S. Cl. .......................... 514/603; 514/171; 514/179; 514/182
[58] Field of Search ................... 514/603, 171, 514/179, 182

[56] References Cited

U.S. PATENT DOCUMENTS 5,556,847 9/1996 Johnson et al. .......................... 514/178
5,567,831 10/1996 Li .......................... 554/43

FOREIGN PATENT DOCUMENTS 9304687 3/1993 WIPO.
9307877 4/1993 WIPO.

*Primary Examiner*—William R. A. Jarvis
*Attorney, Agent, or Firm*—Diane R. Meyers; Arnold B. Silverman; Eckert Seamans Cherin & Mellott, LLC

[57] ABSTRACT

This invention discloses a method for enhancing memory in a patient comprising administering a compound of formula

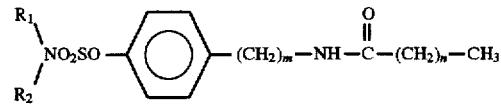

wherein $R_1$ and $R_2$ are independently selected from the group consisting of hydrogen and a lower alkyl group; m is an integer between about 0 and 4; and n is an integer between about 5 and 14. The methods generally comprise administering an effective amount of the compound. The invention also discloses the enhancement of memory by the use of non-steroidal sulfatase inhibitors of the above formula in conjunction with the naturally occurring neurosteroids dehydroepiandrosterone sulfate (DHEAS) and/or pregnenolone sulfate (PS). The patients benefitting from the methods of the present invention will generally have an illness that causes memory loss, or will be individuals who otherwise want to improve memory.

18 Claims, 3 Drawing Sheets

METHODS FOR EFFECTING MEMORY ENHANCEMENT MEDIATED BY NON-STEROIDAL SULFATASE INHIBITORS

BACKGROUND OF THE INVENTION

1. Field of the Invention

This invention relates to methods for memory enhancement in patients suffering from illnesses that effect the memory, such as amnesia, head injuries, Alzheimer's disease, epileptic dementia, presenile dementia, post traumatic dementia, senile dementia, vascular dementia and post-stroke dementia. These methods can also be used for individuals otherwise seeking to enhance their memory. More particularly, the invention relates to the enhancement of memory by non-steroidal sulfatase inhibitors, specifically (p-o-sulfamoyl)-N-alkanoyl p-hydroxyphenylamine compounds.

2. Description of the Background Art

The term "neurosteroids" as will be appreciated by one skilled in the art, and as used herein, refers to steroids synthesized in the brain, either de novo from cholesterol or by in situ metabolism of precursors in the blood. Neurosteroids are concentrated within and are known to produce effects mediated by the central nervous system (CNS). Neurosteroids produce these effects by acting through specific receptors responsible for regulating the conductance of ions, for example potassium ions ($K^+$), sodium ions ($Na^+$) and chloride ions ($Cl^-$), across neuronal cell membranes.

Among the effects associated with neurosteroids is the enhancement of memory. Although the mechanism of this enhancement is not well understood, it is believed that sulfated neurosteroids that enhance memory, such as dehydroepiandrosterone sulfate (DHEAS) and pregnenolone sulfate (PS), inhibit the actions mediated by the $\gamma$-aminobutyric acid ($GABA_A$) receptor, and potentiate the glutamate-induced N-methyl-D-aspartate (NMDA) receptor-mediated response. The $GABA_A$ receptor is an oligomeric protein complex that, when activated by agonists such as GABA or muscimol, produces an increase in neuronal membrane conductance of $Cl^-$; this results in membrane hyperpolarization and reduced neuronal excitability. Thus, engagement of the $GABA_A$ receptor has a sedation effect. In contrast, when NMDA receptors are engaged an excitatory or stimulatory effect is realized. Stimulation of the NMDA receptors stimulates the hippocampus—the portion of the brain responsible for memory function. Increasing the concentration of DHEAS, PS or other sulfated neurosteroids that stimulate the NMDA receptor and/or inhibit the $GABA_A$ receptor, therefore, has the effect of stimulating or enhancing the memory.

The unsulfated analogs of DHEAS, dehydroepiandrosterone (DHEA), and PS, pregnenolone (P), enhance memory, but can also be metabolized to a neurosteroid which has the opposite effect of DHEAS and PS at the $GABA_A$ receptor. The sulfated forms of dehydroepiandrosterone and pregnenolone are therefore preferred for the purpose of memory enhancement.

Patent Application No. PCT/US92/07739 discloses methods for modulating NMDA-mediated ion transport and inhibiting non-NMDA glutamate-induced ion transport in neuronal cells. The methods involve contacting a neuronal cell with an effective amount of the neurosteroid pregnenolone sulfate (PS) or its pharmacologically effective derivatives. Patent Application No. PCT/US92/08935 discloses a method of memory enhancement using pregnenolone and pregnenolone sulfate.

The use of steroidal sulfatase inhibitors for memory enhancement was reported in U.S. Pat. No. 5,556,847. Some steroidal sulfatase inhibitors, however, metabolize in the body to form estrogen. The present invention, in contrast, is directed to non-steroidal sulfatase inhibitors. There remains a very real and substantial need for such a non-steroidal sulfatase inhibitor which can be used to enhance memory.

SUMMARY OF THE INVENTION

The present invention has met the above-described need. The present invention provides methods for using non-steroidal sulfatase inhibitors as described herein for memory enhancement. These sulfatase inhibitors have the formula:

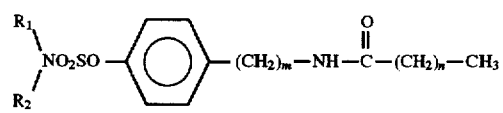

wherein $R_1$ and $R_2$ are independently selected from the group consisting of hydrogen and a lower alkyl group; m is an integer between about 0 and 4; and n is an integer between about 5 and 14. The methods generally comprise administering an effective amount of the compound to a patient.

It is an object of this invention to employ the non-steroidal sulfatase inhibitors described herein in a dosage effective for substantially enhancing the memory function.

It is an object of the present invention to employ non-steroidal sulfatase inhibitors for use in therapeutically treating a patient.

It is a further object of this invention to employ an effective dosage of DHEAS with the non-steroidal sulfatase inhibitors of this invention for substantially enhancing the memory function.

It is yet another object of this invention to use non-steroidal sulfatase inhibitors to increase the concentration of endogenous sulfated neurosteroids by inhibiting sulfatase activity.

It is a further object of the present invention to employ a non-steroidal sulfatase inhibitor that rapidly builds up a high concentration of excitatory neurosteroids in the body.

These and other objects of the invention will be more fully understood from the drawings and the following description of the invention and the claims appended hereto.

DESCRIPTION OF THE PREFERRED EMBODIMENTS

Figure 1:
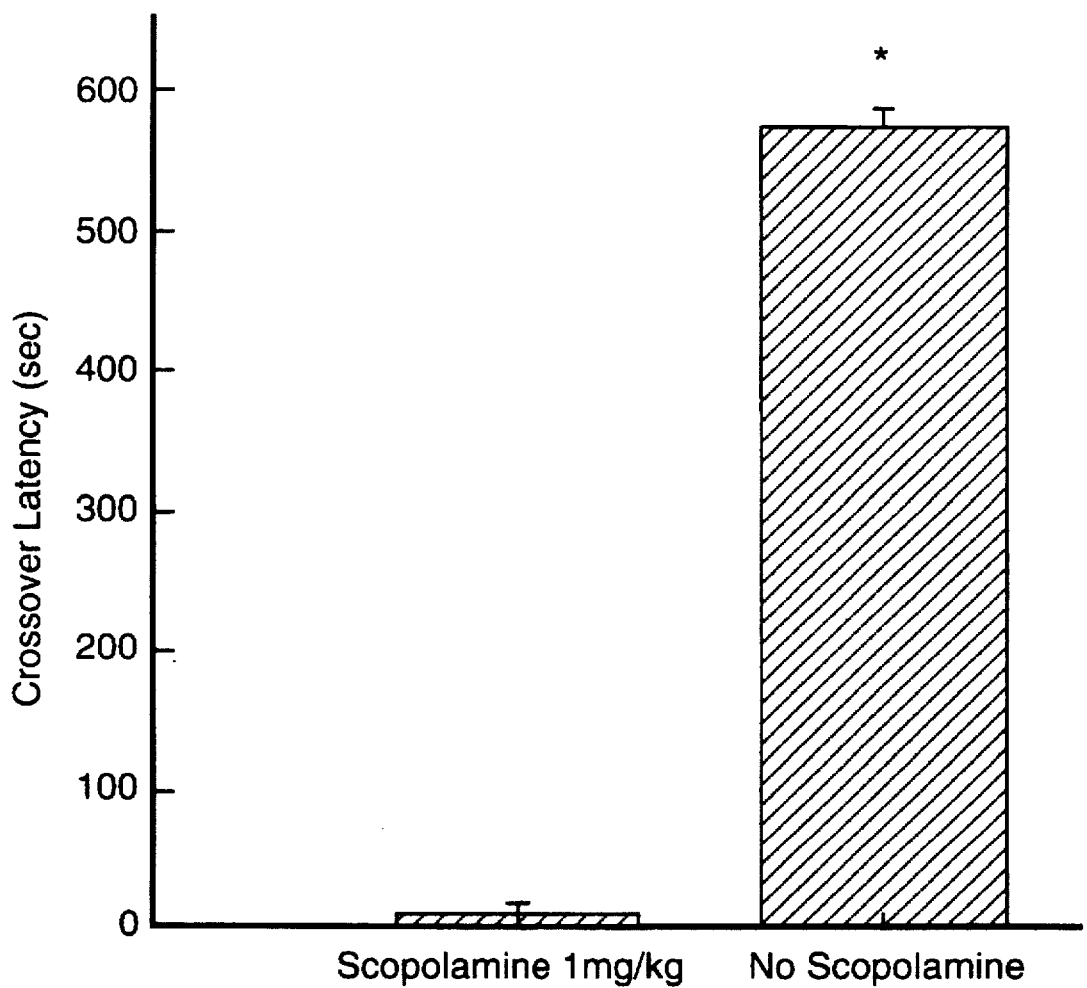
FIG. 1 graphically represents the effect of scopolamine amnesia as measured by crossover latency.

As used herein, the term "patient" refers to members of the animal kingdom including, but not limited to, human beings.

The present invention is directed to a method for enhancing the memory of a patient comprising administering to said patient an effective amount of a compound, or pharmaceutically acceptable salts thereof, having the formula:

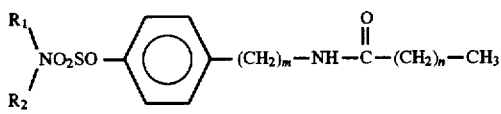

wherein $R_1$ and $R_2$ are independently selected from the group consisting of hydrogen and a lower alkyl group; m is an integer between about 0 and 4; and n is an integer between about 5 and 14. The methods of treating a patient generally comprise administering an effective amount of the compound to the patient.

The lower alkyl groups have between 1 and 6 carbons and can be branched or unbranched. In a preferred embodiment, $R_1$ is H, $R_2$ is H, m is 0 and n is 13, in a more preferred embodiment, $R_1$ is H, $R_2$ is H, m is 2 and n is 11, and in a most preferred embodiment, $R_1$ is H, $R_2$ is H, m is 2 and n is 12.

The present invention is further directed to a method for enhancing the memory of a patient comprising administering to said patient an effective amount of dehydroepiandrosterone sulfate, pregnenolone sulfate or a combination thereof, together with a compound, or pharmaceutically acceptable salts thereof, having the formula:

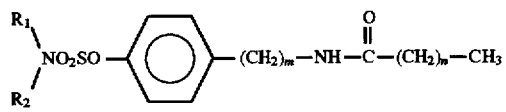

wherein $R_1$ and $R_2$ are independently selected from the group consisting of hydrogen and a lower alkyl group; m is an integer between about 0 and 4; and n is an integer between about 5 and 14. The methods generally comprise administering an effective amount of the compound with either DHEAS, PS or both.

The patients treated by the methods of the present invention can be afflicted with an illness, or can otherwise desire to enhance their memory. "Illness", as used herein, refers to any illness in which memory is impaired, including but not limited to amnesia, head injuries, Alzheimer's disease, epileptic dementia, presenile dementia, post traumatic dementia, senile dementia, vascular dementia and post stroke dementia. The present invention retards or delays the memory loss associated with these illnesses.

The non-steroidal sulfatase inhibitor compounds of the present invention are believed to provide memory enhancing effects by altering the equilibrium between the endogenous sulfated and unsulfated form of the neurosteroids that occur naturally in the brain, although the inventors do not wish to be bound by this mechanism. This alteration is effected by inactivating the sulfatase that converts DHEAS to DHEA, and PS to P, therefore inhibiting the metabolism of the sulfated forms of DHEAS or PS to the unsulfated forms (DHEA or P). It is believed that the sulfatase inhibitors covalently bind to the enzyme thereby rendering the enzyme non-functional or inactive. DHEAS and PS, as discussed above, inhibit the actions mediated by the $GABA_A$ receptor and potentiate the actions mediated by NMDA receptor in the brain. Thus, by maintaining effective levels of DHEAS and/or PS, NMDA receptors are stimulated and/or $GABA_A$ receptors are inhibited and enhanced memory is realized.

DHEAS and PS are naturally occurring neurosteroids manufactured by the body. As will be understood by one skilled in the art, however, DHEAS and PS can also be introduced from external sources. Both DHEAS and PS are commercially available from Sigma Chemical Corp., St. Louis, Mo. The methods of the present invention are therefore enhanced by the use of additional neurosteroids—that is, DHEAS and/or PS introduced from external sources. The use of the compounds of the present invention in conjunction with DHEAS and/or PS results in a higher, sustainable concentration of DHEAS and/or PS than when the compounds of the present invention are used in conjunction with the DHEAS and/or PS produced by the body alone. The dosage and form of the neurosteroids administered to a patient can easily be determined by one skilled in the art. Suitable doses of DHEAS, for example, have been found to be in the range of 0.1 to 10 mg/kg of body weight, preferably 1.0 mg/kg, administered parenterally. Administration of the neurosteroid can be at any time, but is preferably after administration of the sulfatase inhibitor.

The compounds of the present invention can be incorporated in a suitable pharmaceutical carrier prior to being administered to a patient. As used herein, the term "suitable pharmaceutical carrier" refers to any pharmaceutical carrier known in the art that does not have compatibility problems with the compounds of the present invention. Suitable pharmaceutical carriers include, but are not limited to corn oil and light mineral oil, with corn oil being preferred. The preferred ratio of sulfatase inhibitor to carrier is about 1 mg/ml, although other ratios are within the scope of the invention. The compounds of this invention incorporated into the pharmaceutical carrier may then be administered to a patient by parenteral injection, such as for example, intravenously, intrathecally, intramuscularly or intraarterially. Other potential routes of administration include, for example, orally, transdermally or by other means. Parenteral administration is preferred. If oral administration is effected, capsule form is preferred.

The dosage, route, administration, and duration of therapy with the compounds of this invention can be readily determined by those skilled in the art, and will be individualized according to such factors as the illness being treated, body weight of the patient, other therapy employed in conjunction with the compounds of this invention and the condition, clinical response and tolerance of the patient.

Generally, the methods of the present invention are effected by administering an effective amount of the compound described above, either alone or in conjunction with DHEAS and/or PS, to the patient. "Effective amount" refers to that amount of a compound needed to bring about a desired result, such as that amount of the sulfatase inhibitor of the present invention needed to halt or retard the effect of the sulfatase which converts DHEAS to DHEA and PS to P so that therapeutic levels of DHEAS and PS can be accumulated in the body. The effective amount needed for each patient can be determined by one skilled in the art based upon the factors discussed above.

The methods of the present invention are further characterized as establishing a relatively high concentration of the sulfated neurosteroid in the body in a relatively short period of time. Blood level concentrations can be determined by any means known in the art. In addition, a relatively rapid response is seen. For example, a single dose of about 30 mg/kg of the sulfatase inhibitor described herein can inhibit greater than 95% of sulfatase after 24 hours. After 15 days of treatment, the sulfatase activity in the whole body is effectively inhibited, including 95% inhibition in the liver and 86% inhibition in the brain.

The methods of the present invention can be employed to therapeutically treat a patient who is exhibiting signs of memory loss due to illness. Such treatment retards the memory loss associated with these illnesses. Generally, the memory enhanced by the present invention is the "short-term" or acquisition memory. This refers to the ability to accumulate new memories. Thus, the methods of the present invention relieve the symptoms of memory impairing illnesses so that the patients effected with these illnesses can function at a higher level for a longer period of time.

A method for preparing the compounds of the present invention comprises adding alkanoyl chloride dropwise into a cooled solution of p-hydroxyphenylamine and triethyl amine to form a first mixture. Any alkanoyl chloride can be used, preferably one having the formula

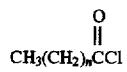

wherein n is between about 5 and 14. The first mixture is then stirred, preferably at room temperature, and extracted to give a first product, N-alkanoyl-p-hydroxyphenylamine. The extraction can be performed in any acidic solution; an HCl solution is preferred. The first mixture can be further treated by separating, drying and concentrating the product under reduced pressure to yield the first product. A hydride and a sulfonamide are then added to the first product to form a second mixture. Sodium hydride and chlorosulfonamide are preferred for the formation of the second mixture. The second mixture is then stirred, preferably at room temperature, and added to a basic solution. The second mixture is then extracted to yield (p-o-sulfamoyl)-N-alkanoyl p-hydroxyphenylamine. Preferably, sodium bicarbonate is added to the second mixture, and the extraction carried out with methylene chloride. The second mixture can be further treated by separating, drying and concentrating the product under reduced pressure to yield the p-hydroxyphenylamine product. Methods for preparing compounds are further presented in the examples below.

EXAMPLES

The following examples are set forth to illustrate the invention and should not be construed as limiting the invention in any way.

Example I

N-nonanoyl tyramine was prepared by adding dropwise about 2.74 moles of nonanoyl chloride to a cooled solution comprising about 1.0 g tyramine and about 2.03 ml of triethylamine in 35 ml of tetrahydrofuranol (THF). The reaction mixture was stirred at room temperature for 48 hours. It was then poured into about 70 ml of 10% HCl solution and the mixture extracted with ethyl acetate (3×50 ml). The ethyl acetate layer was separated, dried (MgSO$_4$) and concentrated under reduced pressure to give a crude N-nonanoyl tyramine product. The product was purified by chromatography on a silica gel column eluted with methylene chloride/ethyl acetate (30:1).

About 173 mg of NaOH was added to a stirred solution comprising about 1 g N-nonanoyl tyramine in 20 ml of anhydrous DMF at 0° C. under nitrogen. The solution was stirred for 30 minutes and about 832 mg of chlorosulfonamide was added in one portion. The solution was then stirred at room temperature for 24 hours. The mixture was poured into a cold saturated sodium bicarbonate solution and the resulting solution was extracted with methylene chloride (3×50 ml). The organic layer was separated, dried (MgSO$_4$) and concentrated under reduced pressure to give a light yellow solid product. The product was purified by chromatography on a silica gel column eluted with methylene chloride/ethyl acetate (20:1). The product produced is (p-o-sulfamoyl)-N-nonanoyl tyramine.

Example II

N-tridecanoyl tyramine was prepared by adding dropwise about 2.80 ml of tridecanoyl chloride to a cooled solution comprising about 1 g of tyramine and about 1.52 ml of triethylamine in THF. The reaction mixture was stirred at room temperature for 48 hours. The mixture was then poured into about 70 ml of a 10% HCl solution and the mixture extracted with ethyl acetate (3×50 ml). The ethyl acetate layer was separated, dried (Na$_2$SO$_4$) and concentrated under reduced pressure to yield about 2 g of crude N-tridecanoyl tyramine. The product was purified by chromatography on a silica gel column eluted with methylene chloride/ethyl acetate (30:1). About 1 g of N-tridecanoyl tyranine was added to a stirred solution comprising about 152 mg of N-tridecanoyl tyramine, sodium hydroxide in 20 ml anhydrous DMF at 0° C. under nitrogen. The solution was stirred for 30 minutes; about 1 g of chlorosulfonamide was slowly added in one portion. The solution was then stirred at room temperature for 24 hours. After this time, the mixture was poured into a cold saturated sodium bicarbonate solution and the resulting solution was extracted with methylene chloride (3×50 ml). The organic layer was separated, dried (Na$_2$SO$_4$) and concentrated under reduced pressure to yield about 677 mg of product, which was then purified by chromatography on a silica gel column eluted with methylene chloride/ethyl acetate (20:1). The product produced is (p-o-sulfamoyl)-N-tridecanoyl tyramine.

Example III

A compound having the general formula described above, wherein R$_1$ is H, R$_2$ is H, m is 2 and n is 12, referred to herein as DU-14, was tested for memory enhancing ability.

Male rats weighing between 80 and 100 grams were purchased from Hilltop Lab Animals Inc. (Scottdale, Pa.) and housed in hanging wire mesh cages in groups of three with water and rat chow available. The room in which the animals were housed was controlled for both temperature and humidity, and there was a standard 12 hour, light/dark cycle. To assess memory, the Gemini Avoidance System (San Diego Instruments) was utilized in a standard passive avoidance paradigm. Briefly, the avoidance apparatus consisted of a box (53×53×32 cm) with two compartments connected by an opening with a sliding door. The room in which the rat was placed was brightly lit, while the other room was dark. Initially, the animals were allowed to explore the apparatus and were then removed. During the memory acquisition trial, animals were placed in the lighted compartment. When an animal entered the dark compartment, the sliding door closed and a mild foot shock (1 mA; 1 sec.) was delivered. The rat was then removed from the apparatus and returned to its cage. Twenty-four hours later the rat was again placed in the lighted side of the apparatus and the time latency to crossing to the dark room recorded. If the rat did not enter the dark room within 10 minutes it was removed from the apparatus. The acquisition of memory for the foot shock was assessed as an increased latency period before entering the dark room on the second day. Significant differences in crossover latency were determined by statistical analysis utilizing one-way analysis of a variance with a Dunnett's test post hoc. Significant differences between groups were interpreted as differences in memory acquisition resulting from the various treatments.

To determine the effect of DHEAS on memory, one hour before the acquisition trial six groups of ten animals were injected intraperitoneally (IP) with one of the following several doses of DHEAS (0, 5, 10, 20, 30, 50, 70 mg/Kg/ml) dissolved in saline. All animals in a given group were administered the same dosage. Thirty minutes prior to testing, the animals were also injected IP with scopolamine (1 mg/Kg) that preliminary studies determined would produce amnesia in this paradigm. Twenty-four hours later the rats were again placed in the apparatus and the time delay before the animals entered the dark compartment was recorded.

To determine whether DU-14 could potentiate the reversal of scopolamine-induced amnesia by DHEAS, groups of ten rats per group were administered IP with DU-14 (10 mg/Kg) suspended in corn oil 48 hours before the acquisition trial. On the day of the acquisition the six groups of trial animals were administered DHEAS and scopolamine as above, except that the dosage range of DHEAS was reduced (0, 0.03, 1.0, 3.0, 10.0 mg/Kg). Twenty-four hours later, crossover latency (the time delay before the rats crossed to the dark compartment) for the groups was determined.

In order to determine whether DU-14 alone could enhance memory, two groups of rats (10 animals per group), were injected with DU-14 (30 mg/Kg; IP), either four hours before the acquisition trial, or daily for 15 days before the acquisition trial. Twenty-four hours following the acquisition trial crossover latency was determined. The daily dosage of DU-14 was 30 mg/kg which inhibited the sulfatase enzyme for about three to four days. The reversal of the amnestic effect of scopolamine was tested 24 hours later.

In a preliminary study, control animals administered saline one hour before the acquisition trial with no scopolamine had a prolonged retention latency the second day (583.8±16.2 sec), indicating a memory of the foot shock from the previous day. Rats administered saline one hour before the amnestic agent scopolamine (1 mg/Kg; IP) 30 minutes before the acquisition trial had a retention latency 24 hours later of only 21.1±10.9 sec indicating a failure to remember the aversive event of the previous day (FIG. 1).

Figure 2:
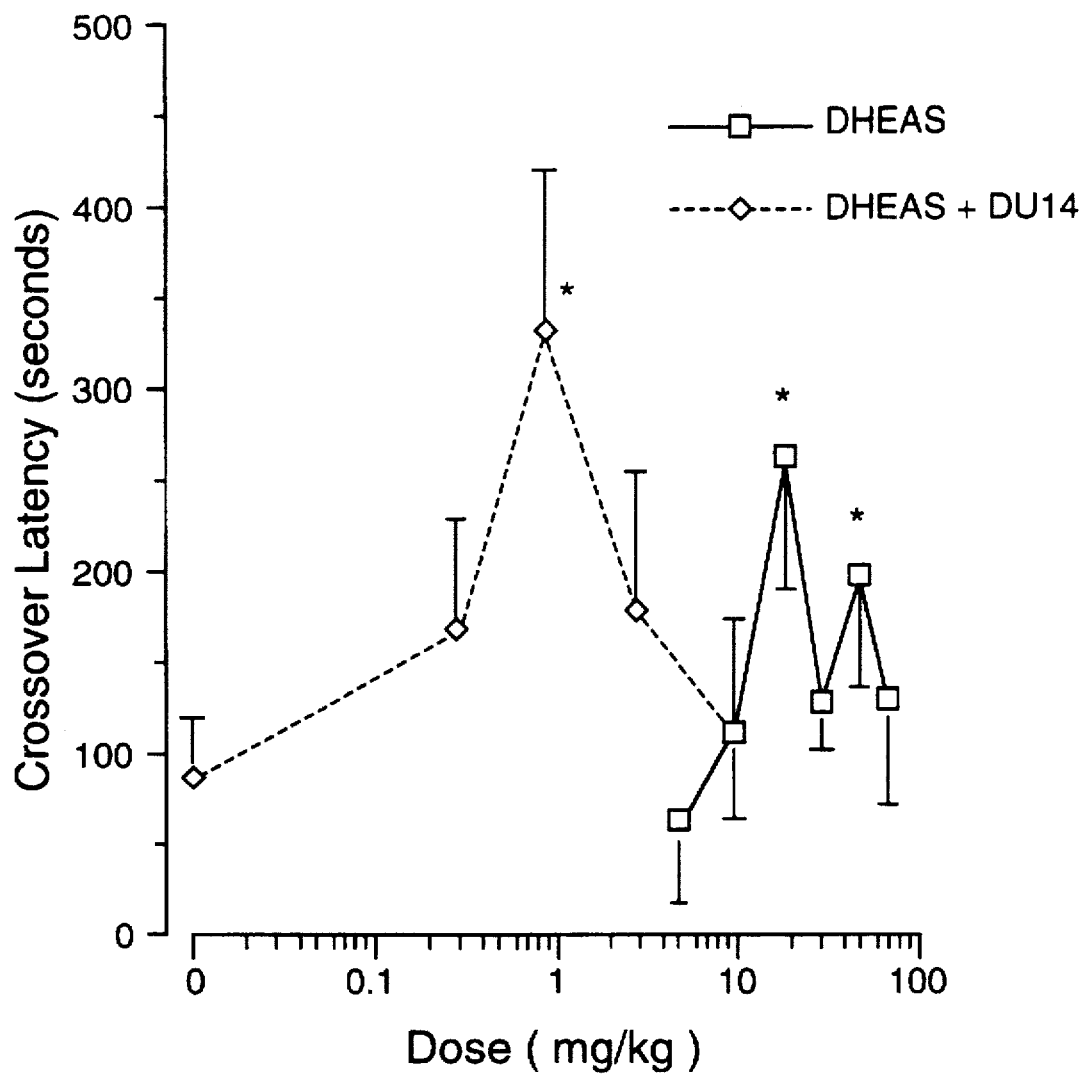
FIG. 2 shows the effect of DHEAS and the effect of DHEAS plus the non-steroidal sulfatase inhibitor of the present invention, referred to as DU-14, on scopolamine induced amnesia in rats.

In the groups of animals administered DHEAS (IP) in various doses (5–70 mg/kg as administered before) one hour before the acquisition trial and scopolamine 30 minutes before, there was a significant ($p \leq 0.05$), reversal of scopolamine-induced amnesia which followed a bell shaped dose response curve (FIG. 2). The maximum effect occurred at 20 mg/Kg DHEAS with a crossover latency of 262.5±84.6 sec. For those groups of animals treated with both DU-14 and DHEAS, there was an increase in the potency of DHEAS with a maximum crossover latency of (331.8±96.4 sec at 1 mg/Kg). This result is shown in FIG. 2 in that the bell curve is shifted to the left.

Figure 3:
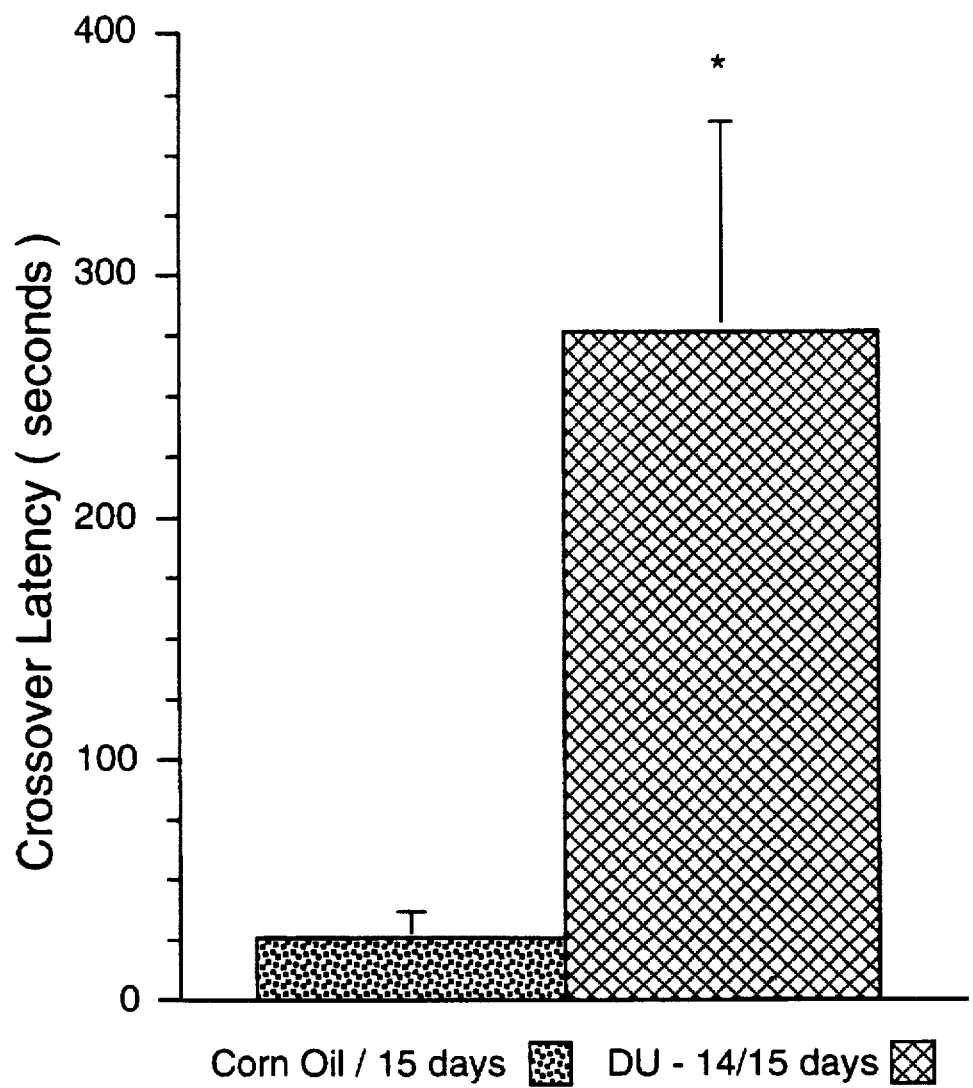
FIG. 3 graphically represents the effect of DU-14 on scopolamine-induced amnesia as measured by crossover latency.

In those groups treated with DU-14 alone, as a single dose DU-14 failed to increase crossover latency. However, in the groups administered DU-14 daily for 15 days before the acquisition trial there was a significant ($p \leq 0.05$) reversal of scopolamine-induced amnesia with a crossover latency of 278.7±88.1 (FIG. 3).

The above results demonstrate a significant increase in crossover latency, which indicates a reversal of scopolamine-induced amnesia, as a result of DU-14.

Example IV

DU-14 was tested for its sulfatase inhibition in rats. 30 mg/kg of the compound was administered to rats IP for 15 days. Sulfatase inhibition was measured by the sulfatase activity in ng $E_1S/\mu g$ protein/hr in the liver and brain as determined by methods known in the art. The results are presented below in Tables 1 and 2.

TABLE 1

Liver Sulfatase Activity

| Group | Sulfatase Activity (ng $E_1S/\mu g$ protein/hr)† | % Inhibition |
|---|---|---|
| Corn Oil Control | 164.10 ± 2.5 | — |
| DU-14 -- 1 Day | 7.85 ± 0.65* | 95.2 |
| DU-14 -- 15 Days | 4.01 ± 0.23* | 97.6 |

†Data represents mean ± SEM
*Indicates significance from control; P<0.01

TABLE 2

Brain Sulfatase Activity

| Group | Sulfatase Activity (pg $E_1S/\mu g$ protein/hr)† | % Inhibition |
|---|---|---|
| Corn Oil Control | 3.24 ± 0.32 | — |
| DU-14 -- 1 Day | 2.76 ± 0.27* | 14.8 |
| DU-14 -- 15 Days | 0.48 ± 0.10* | 85.2 |

†Data represents mean ± SEM
*Indicates significance from control; P<0.01

As can be seen in Table 1, sulfatase inhibition in the liver decreased dramatically after only 1 day, from about 164 to about 8. After 15 days, the sulfatase inhibition was almost 98%. Thus, DU-14 was effective in inhibiting nearly all of the liver sulfatase activity. Sulfatase activity also decreased in the brain after only 1 day, and then by more than 85% after 15 days. DU-14 was therefore successful in effectively inhibiting sulfatase activity in both the liver and the brain.

Both the transported compound and the compound of this invention will be active in the central nervous system after crossing the blood-brain barrier.

It will be understood that the present invention provides methods for memory enhancement comprising administering to a patient a non-toxic (p-o-sulfamoyl)-N-alkanoyl p-hydroxyphenylamine compound. These compounds function as non-steroidal sulfatase inhibitors, serving to maintain or increase the levels of DHEAS and/or PS in the CNS, which in turn promotes memory enhancement.

Whereas particular embodiments of this invention have been described above for purposes of illustration, it will be evident to those skilled in the art that numerous variations of the details of the present invention may be made without departing from the invention as defined in the appended claims.

We claim:

1. A method for enhancing the memory of a patient comprising administering to said patient an effective amount of a compound, or pharmaceutically acceptable salts thereof, having the formula:

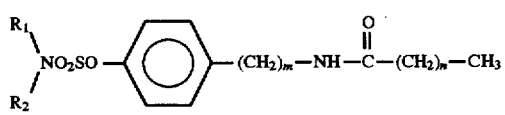

wherein $R_1$ and $R_2$ are independently selected from the group consisting of hydrogen and a lower alkyl group; m is an integer between about 0 and 4; and n is an integer between about 5 and 14.

2. The method of claim 1, wherein said compound is incorporated in a suitable pharmaceutical carrier prior to administration to said patient.

3. The method of claim 2, wherein said suitable pharmaceutical carrier is corn oil.

4. The method of claim 2, wherein said compound is administered orally, subcutaneously, intravenously, intrathecally or intraparenterally.

5. The method of claim 1, wherein said patient has an illness selected from the group consisting of amnesia, head injuries, Alzheimer's disease, epileptic dementia, presenile dementia, post-traumatic dementia, senile dementia, vascular dementia and post stroke dementia.

6. The method of claim 1, wherein said memory is short term memory.

7. The method of claim 1, wherein $R_1$ is H, $R_2$ is H, m is 2 and n is 12.

8. The method of claim 1, wherein $R_1$ is H, $R_2$ is H, m is 2 and n is 11.

9. The method of claim 1, wherein $R_1$ is H, $R_2$ is H, m is 0 and n is 13.

10. A method for enhancing the memory of a patient comprising administering to said patient an effective amount of dehydroepiandrosterone sulfate, pregnenolone sulfate or a combination thereof, together with a compound, or pharmaceutically acceptable salts thereof, having the formula

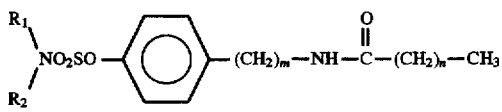

wherein $R_1$ and $R_2$ are independently selected from the group consisting of hydrogen and a lower alkyl group; m is an integer between about 0 and 4; and n is an integer between about 5 and 14.

11. The method of claim 10, wherein said compound is incorporated in a suitable pharmaceutical carrier prior to administration to said patient.

12. The method of claim 11, wherein said suitable pharmaceutical carrier is corn oil.

13. The method of claim 11, wherein said compound is administered orally, subcutaneously, intravenously, intrathecally or intraparenterally.

14. The method of claim 10, wherein said patient has an illness selected from the group consisting of amnesia, head injuries, Alzheimer's disease, epileptic dementia, presenile dementia, post-traumatic dementia, senile dementia, vascular dementia and post stroke dementia.

15. The method of claim 10, wherein said memory is short term memory.

16. The method of claim 10, wherein $R_1$ is H, $R_2$ is H, m is 2 and n is 12.

17. The method of claim 10, wherein $R_1$ is H, $R_2$ is H, m is 2 and n is 11.

18. The method of claim 10, wherein $R_1$ is H, $R_2$ is H, m is 0 and n is 13.

* * * * *